(12) United States Patent
Gulcher

(10) Patent No.: US 9,205,233 B2
(45) Date of Patent: Dec. 8, 2015

(54) BALLOON CATHETER

(75) Inventor: Manfred Gulcher, Raesfeld-Erie (DE)

(73) Assignee: QualiMed Innovative Medizinprodukte GmbH (DE)

( * ) Notice: Subject to any disclaimer, the term of this patent is extended or adjusted under 35 U.S.C. 154(b) by 412 days.

(21) Appl. No.: 13/499,140

(22) PCT Filed: Oct. 1, 2010

(86) PCT No.: PCT/EP2010/005998
§ 371 (c)(1),
(2), (4) Date: May 3, 2012

(87) PCT Pub. No.: WO2011/038928
PCT Pub. Date: Apr. 7, 2011

(65) Prior Publication Data
US 2012/0226339 A1    Sep. 6, 2012

(30) Foreign Application Priority Data

Oct. 1, 2009 (DE) .......................... 10 2009 047 925

(51) Int. Cl.
*A61F 2/06* (2013.01)
*A61M 25/10* (2013.01)
*A61F 2/954* (2013.01)
*A61F 2/958* (2013.01)
*A61F 2/07* (2013.01)

(52) U.S. Cl.
CPC ............ *A61M 25/1011* (2013.01); *A61F 2/954* (2013.01); *A61F 2/958* (2013.01); *A61F 2/07* (2013.01); *A61F 2002/065* (2013.01); *A61M 2025/1045* (2013.01); *A61M 2025/1061* (2013.01)

(58) Field of Classification Search
USPC ......... 606/108, 191–192, 194–195; 623/1.11, 623/1.13–1.14, 1.23, 1.35, 1.36
See application file for complete search history.

(56) References Cited

U.S. PATENT DOCUMENTS

| | | | | |
|---|---|---|---|---|
| 5,639,278 | A * | 6/1997 | Dereume et al. | 623/1.13 |
| 5,820,595 | A * | 10/1998 | Parodi | 604/101.05 |
| 6,299,634 | B1 * | 10/2001 | Bergeron | 623/1.1 |
| 7,476,243 | B2 * | 1/2009 | Eidenschink | 623/1.11 |
| 2001/0002444 | A1 * | 5/2001 | Zilla et al. | 623/1.39 |
| 2002/0143383 | A1 * | 10/2002 | Parodi | 623/1.11 |
| 2007/0078505 | A1 * | 4/2007 | Dimitrov | 623/1.11 |
| 2007/0142819 | A1 * | 6/2007 | El-Nounou et al. | 604/509 |

* cited by examiner

*Primary Examiner* — David Eastwood
(74) *Attorney, Agent, or Firm* — Berliner & Associates

(57) ABSTRACT

The invention relates to a balloon catheter for the placement of stent grafts (1) with a proximal (7) and at least one distal balloon (8), a multi-lumen shaft (5a) having one lumen (6) sized to accommodate a guidewire and at least two lumina (5a, 5b) for individually applying hydraulic pressure to the balloons, with lumina (5b, 6) accommodating the guidewire and one or several distally arranged balloons (8) being passed through the proximal balloon (7) and the stent graft (1) being crimped onto the balloons (7, 8).

9 Claims, 2 Drawing Sheets

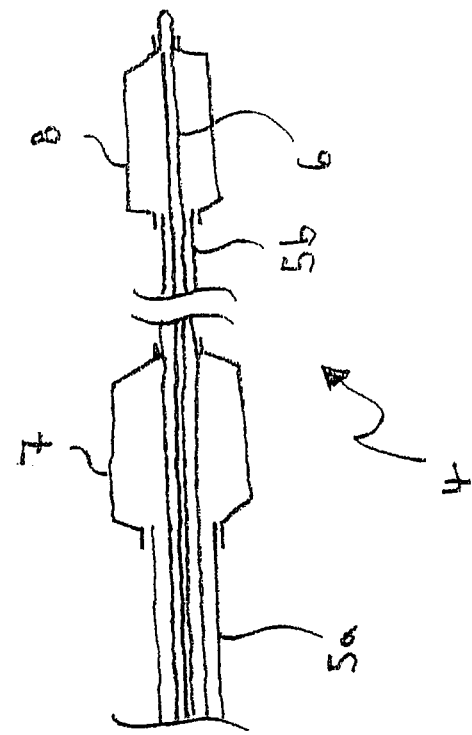
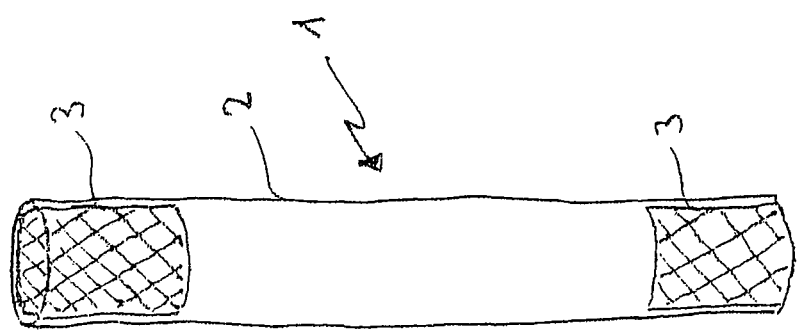

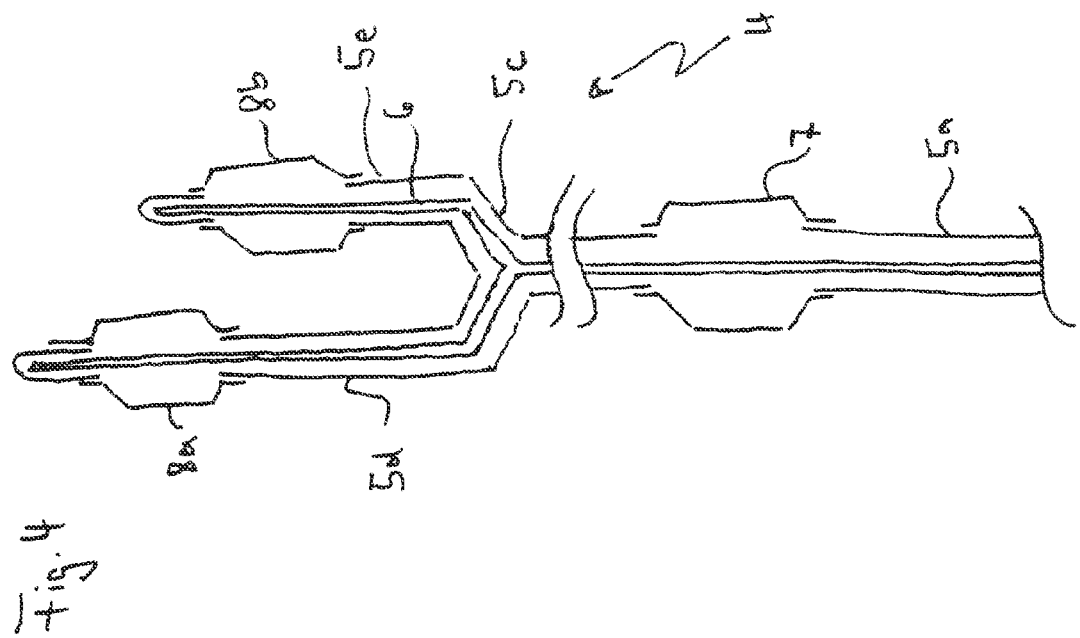
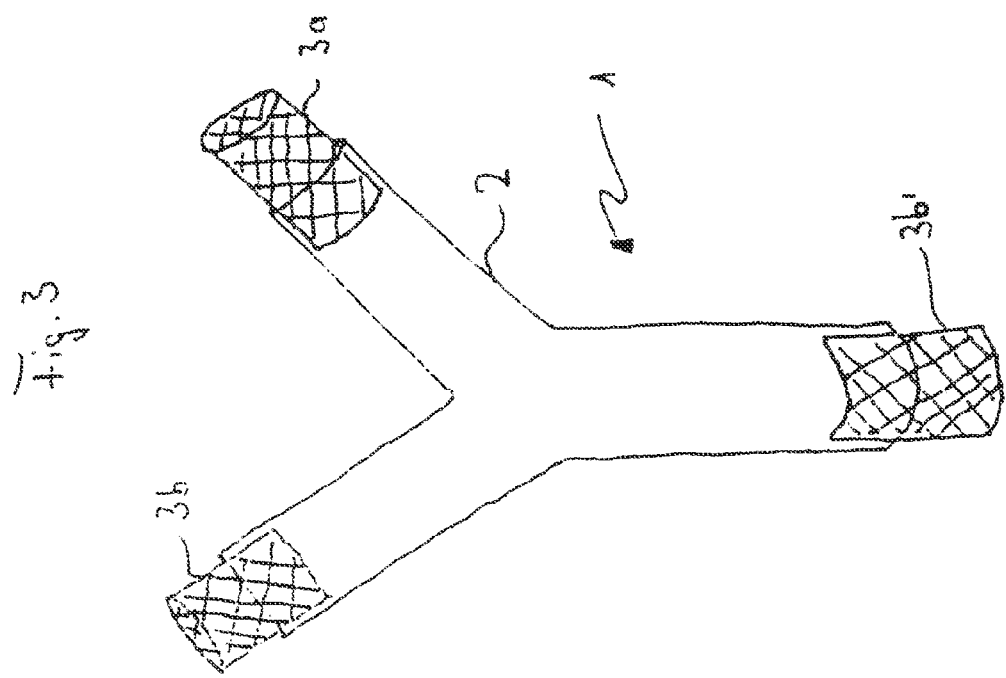

BALLOON CATHETER

The invention relates to a balloon catheter for the placement of stent grafts with a proximal and at least one distal balloon, a multi-lumen shaft having one lumen sized to accommodate a guidewire and at least two lumina for individually applying hydraulic pressure to the balloons.

Aneurysms are dilatations of the blood vessels accompanied by a thinning of the vessel wall. Such alterations of a vessel wall may be congenital or acquired. In the event of severely thinned vessel walls ruptures may be caused through, the pressure of the flowing blood which may entail fatalities or serious effects detrimental to health. This applies in particular to aneurysms occurring in cerebral locations as well as aneurysms in arteries, especially the aorta in the thoracic and abdominal cavities.

Treatment of an existing aneurysm in the chest or abdominal cavities is most frequently administered by way of operative methods in that a vascular prosthesis consisting of Dacron or PTFE (polytetrafluoroethylene) is sewn in, with particular care being necessary not to damage branching-off vessels. In connection with such an operative treatment the case fatality rate is by no means to be underestimated.

Especially in the cerebral region aneurysms are treated by endovascular techniques with the help of catheters enabling the placement of coils consisting of noble metal wire in the aneurysm. Prerequisite for this is that the aneurysm is of aciniform shape and has a narrow access. The noble-metal coil serves to decelerate the flow of blood through the aneurysm, causes a clot to form and results in blocking off and encapsulating the blocked-off aneurysm. It is to be noted, however, that in the event of arterial aneurysms such an approach can only be resorted to very rarely.

Especially for aortic aneurysms it is nowadays also possible to implant so-called stent grafts by endovascular methods. Stent grafts consist of a distal and, if expedient, a proximal stent (as viewed from the attending physician) as well as a tissue-compatible hose or tube element of plastic material. Stent grafts comprising two stents are anchored against the vessel wall by expanding the stent while stent grafts having a distally arranged stent only are sutured to the vessel wall at the proximal end. Although the method is not very stressful for the patient the implants used for the purpose still need to be improved because of leakages that are frequently experienced. Due to these leakages the aneurysm is again subjected to systemic pressure so that the rupturing hazard continues to exist. Moreover, the endovascular placement of such stent grafts by means of traditional catheter techniques is also in need of improvement.

A problem associated with this stent graft is that the stents are made of a self-expanding material, for example nitinol, which means the sealing effect attained is not always sufficient. What is more, the plastic fabric is not always tight enough to rule out the occurrence of micro-leakage. Difficulties relating to the necessity that the side arm has to be attached in the vessel in a complicated manner are also encountered with special Y-shaped implants developed for use with aortic bifurcations and provided with three stents. Here as well leakages occur frequently.

On the other hand, using stent grafts is a very gentle method of blocking off an aneurysm so that enhancing the development of this technology is desirable.

From publication WO 02/028316 A2 a stent graft for the treatment of artery stenosis is known which consists of a conventional stent to which an in-line element has been attached. Such in-line element is made of a biocompatible material, for example PTFE. The stent graft is sutured to the vessel wall proximally to the stent.

A stent graft system suitable for implantation into arterial bifurcations has been described in WO 1999/013808. The implant is comprised of a primary graft with stents arranged at its ends and a centrally located connection element as well as a second graft element provided with connection element and stent, said components being connected to each other at the placement site within the bifurcation. The coupling process is intricate and calls for some degree of skill.

It is thus the objective of the present invention to provide a balloon catheter with a stent graft which can be put to use especially in the region of vessel bifurcations, for example in the aortic bifurcation, comprises the necessary number of balloons to anchor the stents of the graft at the vessel wall and furthermore permits the safe and secure placement of the stent graft. The stent graft shall possess a uniform, leakage-proof, well biocompatible as well as sufficiently firm and secure hose or tube-like connection between the stents.

This objective is reached with a balloon catheter of the kind first mentioned above which provides for the lumina accommodating the guidewire and one or several distally arranged balloons to be passed through the proximal balloon and the stent graft to be crimped onto the balloons.

The balloon catheter in accordance with the present invention can have two balloons, one distally and one proximally arranged balloon, but may also be provided with an additional distal balloon for use with a three-arm stent graft. Such three-arm stent grafts may in particular be applied in the region of the aortic bifurcation.

The inventive balloon catheter has separate lumina through which hydraulic pressure can be exerted and applied to the individual balloons. This enables the sequential application of the stents of the stent graft, with one or several of the distal stents of the graft being placed first, followed by anchoring the proximal stent by having exerted tension on the hose element. For this purpose the lumina for one or several distal stents are passed through the proximal stent and this also applies to the lumen for the guidewire. In case there are two proximal stents it is considered expedient for the lumen accommodating the guidewire to branch off so that the guidewire can separately extend towards and into the two distal balloons. The lumen accommodating the guidewire is as a rule closed distally towards the distal balloons such that, via the guidewire, a certain controlling effect can be produced to act on the balloons even in the form of exerting a certain push/pull effect when restraining the graft.

The stents of the stent graft are customary stents of the kind suitable for placement inside blood vessels either via balloons or in a self-expanding manner. They are normally fabricated of medical steel or nitinol.

The tubular element of the stent graft is made of non-woven fabric material consisting of micro- or nanofibers produced by electrospinning. Such non-woven fabric materials are basically known to those skilled in the art and have been described, for example, in publications WO 02/49536 A2 and WO 03/045875 A1.

The non-woven fabrics as per WO 02/49536 A2 may consist of several layers of electrospun microfibers and have been optimized in terms of their permeability to body fluids.

Basically, all polymers capable of being processed by electrospinning can be used as materials for the non-woven fabric. However, these are in particular polyurethane, polyester and/or polytetrafluoroethylene (PTFE) and, as the case may be, biodegradable plastic materials for example polylactides or polyglycolides or mixed polymers thereof.

Preferably, the non-woven fabric material used is of multilayer design. In particular, a three-layer configuration is used for this non-woven fabric. The individual layers of the non-woven fabric may be composed of the same material but different layer materials may be used as well, for example a combination of micro- and nanofibers of polyurethane and PTFE.

The stent graft is preferably of Y-shape, i.e. it has three ends where stents are located. The stent graft is thus suited for placement in vessel bifurcations, also and especially in the aortic bifurcation in which region abdominal aortic aneurysms are frequently encountered. Such a three-ended stent graft is provided with two distal stents and one proximal stent, said stents being connected with each other through the hose-like non-woven fabric structure.

It is to be noted in this context that the terms "distal" and "proximal" have been selected to denote and refer to the guiding direction of the catheter by means of which the stent graft is implanted. Accordingly, "distal" means that the respective stent is located in the distal area of the insertion catheter whereas a "proximal" stent is arranged at the end of the catheter where the attending physician is positioned.

The non-woven fabric of the hose-like stent graft is spun onto the terminally arranged stents. It is considered expedient for this purpose to integrate the stent at least partially, preferably entirely into the non-woven fabric. In the transitional region between stent and graft it is considered expedient to arrange additional reinforcement layers. By joining the stent to the non-woven fabric by spinning an optimum fabric-to-stent attachment is achieved and, after expansion, a good sealing effect with respect to the vessel wall is brought about.

The invention also relates to a stent graft prepared so as to be ready for application, i.e. a stent graft containing for application stents crimped on the balloons of a balloon catheter. For this purpose the individual balloons can be pressurized separately which enables first one or several of the distal stents to be placed in a vessel and finally the stent which is to be arranged proximally. The catheters to be employed for this purpose will expediently be provided with a multilumen shaft and are otherwise of customary design. In the event of a stent graft having two distal stents and one proximal stent as is employed for aortic bifurcation applications the two distal stents can of course be guided, placed as well as expanded separately. Prerequisite for this is that at a point distally to the proximal stent the balloon catheter branches to form two arms each of which accommodating one balloon.

The invention is elucidated in more detail through the figures showing preferred embodiments and the descriptions of these figures hereinafter where FIG. 1 shows a stent graft provided with two stents;

FIG. 2 depicts a multilumen catheter for the placement of the stent graft according to FIG. 1;

FIG. 3 shows a Y-shaped stent graft for the implantation into vessel bifurcations; and FIG. 4 depicts a multilumen catheter for the placement of the stent graft according to FIG. 3.

FIG. 1 shows a stent graft 1 according to the invention provided with an electrospun non-woven fabric 2 and stents 3 at both ends integrated into the fabric. The stents are entirely spun into the non-woven fabric so that their surface is covered by the fabric. As a result of the elasticity of the non-woven fabric the connection or joint between fabric and stent remains intact when the stent is crimped onto a balloon. The same applies when the expansion occurs during placement in a vessel.

FIG. 2 is a schematic representation showing a balloon catheter 4 with shaft 5, said catheter being made up of a multilumen shaft 5a and a single-lumen shaft 5b. In the middle of the catheter a guidewire lumen 6 is located which accommodates a guidewire, not shown here, which is needed for the placement of the catheter. A proximal balloon 7 and a distal balloon 8 can be separately pressurized hydraulically via the free lumina of shaft 5 so that implant 1 mounted on the configuration, with the stents 3 being crimped onto the balloons 7 and 8, can be endoluminally placed in a vessel with the help of the balloon catheter (dual balloon catheter).

FIG. 3 shows an inventive graft with three stents, with approximately half of each stent being integrated into the non-woven fabric 2. The graft is Y-shaped so that it can be placed in a bifurcation of the vascular system. In the event of an implantation in the aortic bifurcation stent 3b' is the proximal stent which is crimped onto the proximal balloon of the balloon catheter whereas stents 3a and 3b are crimped onto two separate balloons arranged distally to the proximal balloon in the two arms of the balloon catheter as illustrated in FIG. 4. FIG. 4 is a schematic illustration of a catheter 4 provided with a branching point located distally to the proximal balloon 7. Shaft 5a is a multi-lumen shaft through which the lines, (not shown), pass that are required for the hydraulic pressurization of the balloons 7, 8a and 8b. A guidewire lumen 6 passes through the multilumen shaft 5a and branches off in the forking zone 5c of the shaft where it leads into the two arms 5d and 5e. In case of the placement of the implant shown in FIG. 3 the proximal balloon 7 serves the application of the proximal stent 3b' while the distal stents 3a, 3b are crimped onto the balloon 8a and 8b located in arms or branches 5d and 5e. The balloon catheters according to the present invention are for example introduced into the aorta via a guidewire catheter adopting the femoral access technique. In the event of the graft illustrated in FIG. 1 the distal stent is positioned above an aortic aneurysm to be treated and expanded in that location. This results in the distal fixation of the stent and the graft attached to it. Through a slight pull on the system the graft can be slightly tensioned before the proximal stent is expanded.

Placement of the Y-shaped graft in the region of the aortic bifurcation follows the same basic principle with the exception that an additional catheter arm is arranged parallelly to the distal balloon, said arm can be maneuvered during the placement process into the opposite bifurcation branch with the help of the guidewire extending through the respective guidewire lumen. Implantation of the graft is carried out in a manner similar to the variant described before. Initially, the first distal stent is expanded and, when this has been done, tension is exerted on the graft via the catheter arm extending into the bifurcation branch, and the second distal stent is then expanded in that location. Finally, tension is again exerted on the proximal branch of the graft and the proximal stent is expanded.

It is of course also provided that the inventive balloon catheter can be modified in such a manner that the graft has more than one branch. For example, a relevant graft may spread in branches forming three arms. Moreover, it is to be understood that grafts of this kind can be employed not only for the treatment of aortas and the aortic bifurcation but also in other vascular regions.

The invention claimed is:

1. A balloon catheter (4) with a proximal (7) and two distal balloons (8a, 8b), a multi-lumen shaft (5a) having one lumen (6) sized to accommodate a guidewire, lumina for individually applying hydraulic pressure to the balloons (7, 8a, 8b), and a stent graft (1) comprising two distal stents (3a, 3b) and a proximal stent (3b') crimped onto the balloons (7, 8a, 8b) the stents (3a, 3b) being connected with each other through a hose-like textile element (2) said textile element being a non-woven fabric of electrospun micro- or nanofibers and attached to the stents (3a, 3b) by a spinning method, said catheter (4) branching distally from the proximal balloon (7) into two arms (5d,5e) each one having one balloon (8a,8b) and said lumen (6) sized to accommodate the guide wire running within the multi-lumen shaft (5a), branching at a branch point distal of the proximal balloon (7) and leading into the arms (5d, 5e).

2. The balloon catheter according to claim 1, wherein the stent graft is an aortic bifurcation graft (1).

3. The balloon catheter according to claim 1, characterized in that the non-woven fabric is of multi-layer design.

4. The balloon catheter according to claim 1, characterized in that the non-woven fabric is a three-layer non-woven fabric.

5. The balloon catheter according to claim 1, characterized in that the non-woven fabric consists of polyurethane, polyester and/or polytetrafluoroethylene fibers.

6. The balloon catheter according to claim 5, characterized in that the non-woven fabric consists of polyethylene terephthalate fibers.

7. The balloon catheter according to claim 3, characterized in that the multi-layer non-woven fabric contains layers made of different fiber materials.

8. The balloon catheter according to claim 1, characterized by reinforcement layers of the non-woven fabric in transitional regions between stents (3b', 3a, 3b) and the non-woven fabric of the stent graft (1).

9. The balloon catheter according to claim 1, characterized in that the stents (3b', 3a, 3b) are spun at least partially into the non-woven fabric.

\* \* \* \* \*